United States Patent
Mandal et al.

(10) Patent No.: US 11,548,838 B2
(45) Date of Patent: Jan. 10, 2023

(54) PROCESS FOR SYNTHESIS OF POLYHYDROCARBONS AS HEAT TRANSFER AGENTS

(71) Applicant: Indian Oil Corporation Limited, Mumbai (IN)

(72) Inventors: Tanmay Mandal, Faridabad (IN); Krishna Vankudoth, Faridabad (IN); Manisha Saraswat, Faridabad (IN); Ajay Kumar Arora, Faridabad (IN); Vivekanand Kagdiyal, Faridabad (IN); Deepak Saxena, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

(21) Appl. No.: 17/587,042

(22) Filed: Jan. 28, 2022

(65) Prior Publication Data
US 2022/0242804 A1 Aug. 4, 2022

(30) Foreign Application Priority Data
Feb. 2, 2021 (IN) .............................. 202121004501

(51) Int. Cl.
*C07C 2/76* (2006.01)

(52) U.S. Cl.
CPC ............ *C07C 2/76* (2013.01); *C07C 2523/44* (2013.01)

(58) Field of Classification Search
CPC ... C07C 2/76; C07C 2523/44; C07C 2521/18; C07C 1/321; C10M 105/06;
(Continued)

(56) References Cited

U.S. PATENT DOCUMENTS

| 3,210,434 A | 10/1965 | Chapman |
| 2003/0008768 A1* | 1/2003 | Hartwig ................. C07C 1/321 502/103 |
| 2003/0181519 A1* | 9/2003 | Mewshaw ................ A61P 7/12 514/319 |

FOREIGN PATENT DOCUMENTS

| CN | 1133667 C | 1/2004 |
| DE | 2003915 A1 | 8/1971 |

OTHER PUBLICATIONS

J.R. Bell et. al., "Phenylnaphthalene as a Heat Transfer Fluid for Concentrating Solar Power: High-Temperature Static Experiments", ORNL/TM-2012/118, Oak Ridge National Laboratory, May 2012.

(Continued)

*Primary Examiner* — Ali Z Fadhel
(74) *Attorney, Agent, or Firm* — Workman Nydegger

(57) ABSTRACT

The present invention provides a one-pot process of synthesis of phenyl naphthalene compounds that are employed as heat transfer agents. More particularly, the present invention provides a process of preparation of 1-phenylnaphthalene and 2-methyl-1-phenylnaphthalene using refinery spent catalyst. These molecules are known for application as synthetic heat transfer fluids that deliver outstanding performance and thermal stability at continuously high operating temperatures. The reaction is carried out in aqueous medium using a spent catalyst which is a palladium based charcoal catalyst as obtained from various refinery processes. Further, the present invention provides a heat resistant formulation using the synthesized polyhydrocarbons, wherein the formulation is optimized with a free radical scavenger.

14 Claims, 2 Drawing Sheets

(58) Field of Classification Search
CPC ........ C10M 2201/05; C10M 2203/065; C10N 2030/08; B01J 21/18; B01J 23/44; B01J 37/0036; B01J 37/009; B01J 37/04; B01J 37/20; B01J 37/28; C09K 5/10
See application file for complete search history.

(56) References Cited

OTHER PUBLICATIONS

Deo et al., "Synthesis of 1-Phenyl Naphthalene and Pericarbonyl Lignans", Asian Journal of Chemistry, vol. 22, No. 5, Jan. 2010, pp. 3362-3368.
Taherpour et al., "One-pot Solvent-free Catalytic Dimerization Reaction of Phenylacetylene to 1-Phenylnapthalene", Journal Chem. Sci.,vol. 127, No. 9, Sep. 2015, pp. 1523-1530.
Garg et al., "Cross-Coupling Reactions of Aryl Pivalates with Boronic Acids", Journal American Chemical Society, vol. 130, No. 44, Oct. 8, 2008, pp. 14422-14423.
Rajdiputane et al., "Green Approach Towards the Synthesis of 1-Phenyl Napthalene Lignan and their Derivatives", International Journal of Advances in Science Engineering and Technology, ISSN: 2321-9009 Special Issue-1, Jun. 2015.

* cited by examiner

PROCESS FOR SYNTHESIS OF POLYHYDROCARBONS AS HEAT TRANSFER AGENTS

FIELD OF THE INVENTION

The present invention relates to a process of preparation of phenyl naphthalene compounds that are employed as heat transfer agents. More particularly, the present invention relates to a one-pot synthesis of a phenyl naphthalene compound starting from bromonaphthalene derivative, wherein the product obtained is stable at high temperatures.

BACKGROUND OF THE INVENTION

Heat transfer fluids have been identified as one of the crucial components used to improve the efficiency of concentrated solar power plants. Synthesis of poly-hydrocarbon molecules has been a subject of great interest, as it has wide application as heat transfer fluid in solar thermal application. These molecules also serve as important intermediates for synthesis of cyclo lignans for their active physiological properties. Few reports have been found on the synthesis of 1-phenylnaphthalene & 2-methyl-1-phenylnaphthalene.

U.S. Pat. No. 3,210,434 revealed the preparation of 1-phenylnaphthalene from benzene and naphthalene. The process ends up with the formation of both 1-phenylnaphthalene and 2-phenylnaphthalene in a certain ratio at a very high temperature (range 1400-1600° F.). The best conversion was obtained when the benzene/naphthalene are taken in the ratio of 3:2. But they obtained very low yields of 1-phenylnaphthalene and 2-phenylnaphthalene.

J. R. Bell et. al (Web site: http://www.osti.gov/bridge) described in a report ORNL/TM-2012/118 of Oak Ridge National Laboratory that 1-phenylnaphthalene could be used as a heat transfer fluid for concentrating solar power system. This report has shown the synthesis procedure for 1-phenylnaphthalene by a modified Suzuki-Miyaura coupling reaction of 1-Bromonaphthalene with phenyl boronic acid in the presence of palladium acetate & tri-(o-tolyl)phosphine catalyst and potassium carbonate additive in n-propanol to yield 1-phenylnaphthalene in 99% purity by GC.

In Organic Synthesis Collective Volume, it is reported that 1-phenylnaphthalene can be synthesized in multistep process. In the first step α-tetralone undergoes Grignard reaction with phenylmagnesium bromide followed by dehydration using acetic anhydride to generate 1-phenyldialin. In the second step 1-phenyldialin is dehydrogenated in the presence of sulphur at 240-270° C. to produce 1-phenylnaphthalene. The product is finally purified by distillation.

Further, 1-Phenylnaphthalene has been prepared by the Grignard reaction of cyclohexanone with α-bromonaphthalene. The dehydrogenation of the reduced naphthalene has been accomplished by the use of sulfur, bromine, platinum black, or selenium.

Deo et al (*Asian Journal of Chemistry*, Vol. 22, No. 5, 2010, pp. 3362-3368) have described a method for the synthesis of 1-phenylnaphthalene system for use as an important intermediate for synthesis of cyclo lignans. At first α-arylidene β-benzoyl propionic acid is converted to its ester by diazomethane ($CH_2N_2$) to generate methyl α-arylidene β-benzoyl propionic acid which is further cyclized by polyphosphoric acid (PPA) and concentrated sulfuric acid ($H_2SO_4$) to 1-phenylnaphthalene and its derivatives.

Taherpour et al. (*J. Chem. Sci.* Vol. 127, No. 9, 2015, pp. 1523-1530) reported a one-pot solvent-free catalytic dimerization of phenylacetylene to 1-phenylnaphthalene by Cu/C catalyst in darkness and at room temperature. The report discloses the reaction of a mixture of phenylacetylene in presence of the catalyst Cu/C carried out in a dried tube with a small magnetic stirrer bar. The tube was sealed and then stirred overnight at room temperature and in darkness to obtain the catalyst.

Ruchardt and Merz demonstrated the Gomberg-Bachmann (*Tetrahedron Lett.* No. 36, 1964, pp. 2431-2436) process for the preparation of 1-phenyl naphthalene in a very low yield (<40%). In this process naphthylamine reacts with sodium nitrite and hydrochloric acid in benzene. This process was rejected because of the safety aspect of explosive diazo-salt which is the intermediate of this reaction.

Garg and coworkers (*J. Am. Chem. Soc.* Vol. 130, No. 44, 2008, pp. 14422-14423) reported the Suzuki-Miyaura coupling of naphthyl pivalates with phenylboronic acid in the presence of an air-stable Ni(II) complex for the preparation of 1-phenyl naphthalene.

DE2003915A1 discloses a process for preparation of 1-phenyl-naphthalene and 1-phenyl-4-(1'-phenylethyl) naphthalene or mixtures by heating styrene trimer in the presence of dehydrogenating catalysts at 70-600 degrees. Styrene trimer is a by-product of styrene polymerisation. Generally, at lower temperatures 1-phenyl-4-(1'-phenylethyl) naphthalene is produced, while at higher temperatures 1-phenyl-naphthalene is produced. Further, suitable catalysts include metals e.g. Pt, Pd, Ni, Cu, oxides; Zn, Al, Cr, Mo, W, tungsten (IV) sulphide, Cu chromite.

CN1133667C discloses a method of preparation and the application for phenylnaphthalene polymer. The phenylnaphthalene polymer is prepared from naphthalene and benzene in mole ratio of (5-12000):1 in the presence of anhydrous $CuCl_2$ and anhydrous $AlCl_3$ catalyst in mole ratio of (2-8):(8-2). The reaction mixture was stirred in reactor under inert condition at 25-50° C. for 1 to 5 hrs.

Rajdiputane et al. (*International Journal of Advances in Science Engineering and Technology*, ISSN: 2321-9009 Special Issue-1, June 2015) disclosed a green approach for the synthesis of 1-phenyl naphthalene from β-benzoyl propionic acid. It is a three step reaction process. In the first step synthesis of α-arylidine-γ-phenyl δ, β-butenolide performed by Perkin reaction, in second step synthesis of α-arylidine β-benzoyl propionic acid performed by cleavage using alcoholic sodium carbonate and in third step synthesis of 1-phenyl naphthalene carried out by cyclization using PPA (polyphosphoric acid), $H_2SO_4$ (sulphuric acid), sulphamic acid. The structure of 1-phenyl naphthalene has been confirmed by spectral and elemental analysis.

The prior arts available for synthesis of thermal fluids viz. 1-phenylnaphthalene & 2-methyl-1-phenyl naphthalene having following shortcomings:
   Catalysts used in the literature are costly and non-recyclable in nature.
   Different types of organic solvents are used for the preparation of this molecule as reported in the literature which create complexity in the final work up process and adds additional cost to the production.
   One of the reported processes involves requirement of very high reaction temperature (1400-1600° F.).
   Multistep synthesis of 1-phenylnaphthalene is also reported that involves tedious reaction process which is time consuming.

Accordingly, there is a need for an approach that resolves problems of the state of the art in order to provide efficient heat transfer agents for thermal application. Many organic molecules are reported to be used as thermal fluids, but most of them are not stable at high temperature (>400° C.)

application. Most of the inventions in this field heretofore known suffer from the disadvantage of complexity of reaction process, high reaction temperature and use of costly catalysts. So, developments of cost effective thermal fluids based on organic molecules are highly desired for high temperature solar thermal application.

OBJECTIVES OF THE INVENTION

The prime objective of the present invention is to provide a heat transfer agent which is stable at very high temperatures.

Another objective of the present invention is to provide a phenyl naphthalene compound selected from 1-phenylnaphthalene and 2-methyl-1-phenylnaphthalene as a heat transfer agent.

Another objective of the present invention is to provide cost effective thermal fluids based on organic molecules.

Yet another objective of the present invention is to provide a stable formulation of phenyl naphthalenes with optimized dosages of free radical scavenger for use as thermal fluids.

SUMMARY OF THE INVENTION

Accordingly, the present invention provides a process for preparation of thermal fluid for high temperature solar thermal application. The commercially available heat transfer fluids being either not suitable for application above 400° C. or are not cost effective, the present invention provides synthesized polyaromatic molecules prepared in a one pot single step reaction using spent catalyst obtained from other refining processes.

The present invention thus provides a one-pot process for synthesis of a phenyl naphthalene compound, wherein the process comprises:
a) grinding a spent catalyst obtained from a refining process;
b) mixing the spent catalyst with tripotassium phosphate and sodium dodecyl sulfate to obtain a reaction mixture I, wherein molar ratio of mixing the tripotassium phosphate and the sodium dodecyl sulfate ranges from 1:1 to 7:1;
c) adding water to the reaction mixture I followed by stirring to obtain a reaction mixture II;
d) adding phenylboronic acid to the reaction mixture II followed by addition of a bromonaphthalene derivative at room temperature to obtain a reaction mixture III, wherein molar ratio of mixing the phenylboronic acid and the bromonaphthalene derivative ranges from 1:1 to 1.5:1;
e) heating the reaction mixture III followed by vigorous stirring for 4-6 hours; and
f) cooling down to room temperature followed by filtration to separate the catalyst.

Further, the present invention provides a heat resistant formulation comprising the phenyl naphthalene compound obtained from the disclosed process and a free radical scavenger; wherein the free radical scavenger is an iron or cerium based compound.

DESCRIPTION OF THE INVENTION

Figure 1:
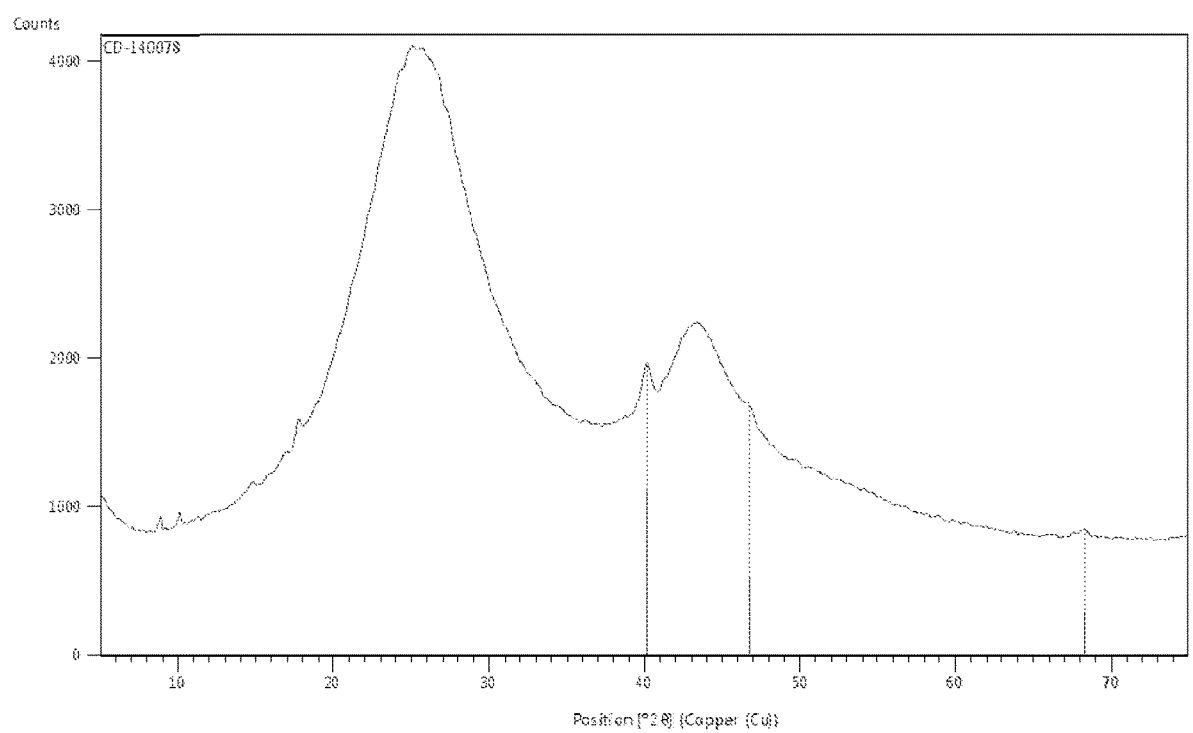
FIG. 1 represents the XRD spectrum of Refinery spent catalyst

For the purpose of promoting an understanding of the principles of the present disclosure, reference will now be made to the specific embodiments of the present invention further illustrated in specific language to describe the same. The foregoing general description and the following detailed description are explanatory of the present disclosure and are not intended to be restrictive thereof. It will nevertheless be understood that no limitation of the scope of the present disclosure is thereby intended, such alterations and further modifications in the illustrated composition, and such further applications of the principles of the present disclosure as illustrated herein being contemplated as would normally occur to one skilled in the art to which the present disclosure relates. Unless otherwise defined, all technical and scientific terms used herein have the same meaning as commonly understood by one ordinarily skilled in the art to which this present disclosure belongs. The methods, products and examples provided herein are illustrative only and not intended to be limiting.

The present invention provides a process for preparation of thermal fluid for high temperature solar thermal application. Accordingly, the present invention provides a process of preparation of 1-phenylnaphthalene and 2-methyl-1-phenylnaphthalene using refinery spent catalyst obtained from various refining processes. These molecules are known for application as synthetic heat transfer fluids. The molecules are resonance stabilized due to the presence of poly-aromatic ring. The present invention provides thermal fluid for use at high temperature (400-500° C.) using refinery spent catalyst and water as solvent medium. The refinery spent catalyst is palladium based on charcoal and is available from refinery unit. The refinery spent catalyst is selected based on characterization using X-ray Diffraction (XRD), X-ray fluorescence (XRF), Molecular spectrum analysis, elemental analysis by ICAP and thermal gravity analysis. High purity yields of the products 1-phenylnaphthalene and 2-methyl-1-phenylnaphthalene are obtained by the optimized process.

The present invention provides a one-pot process of synthesis of a phenyl naphthalene compound, wherein the process comprises:
a) grinding a spent catalyst obtained from a refining process;
b) mixing the spent catalyst with tripotassium phosphate and sodium dodecyl sulfate to obtain a reaction mixture I, wherein molar ratio of mixing the tripotassium phosphate and the sodium dodecyl sulfate ranges from 1:1 to 7:1;
c) adding water to the reaction mixture I followed by stirring to obtain a reaction mixture II;
d) adding phenylboronic acid to the reaction mixture II followed by addition of a bromonaphthalene derivative at room temperature to obtain a reaction mixture III, wherein molar ratio of mixing the phenylboronic acid and the bromonaphthalene derivative ranges from 1:1 to 1.5:1;
e) heating the reaction mixture III followed by vigorous stirring for 4-6 hours; and
f) cooling down to room temperature followed by filtration to separate the catalyst.

In an embodiment, the present invention provides a process wherein in step (e) the reaction mixture III is heated at a temperature ranging from 90-110° C.

In an embodiment, the present invention provides a process of synthesis of 1-phenylnaphthalene and 2-methyl-1-phenylnaphthalene which are polyaromatic molecules and are derivatives of phenylnaphthalene.

In an embodiment, the present invention provides a process of synthesis of 1-phenylnaphthalene wherein the bromonaphthalene derivative in step (d) in the process of preparation of 1-phenylnaphthalene is 1-bromonaphthalene.

In an embodiment, the present invention provides a process of synthesis of 2-methyl-1-phenylnaphthalene wherein the bromonaphthalene derivative in step (d) in the process of preparation of 2-methyl-1-phenylnaphthalene is 1-bromo-2-methylnaphthalene.

In an embodiment, the present invention provides a process of synthesis of a phenyl naphthalene compound wherein the reaction mixture is stirred at a speed ranging from 300-500 rpm.

In another embodiment, the present invention provides a process wherein the spent catalyst is a palladium-carbon based catalyst with palladium content ranging from 0.05 to 0.1 wt % of the catalyst.

In an embodiment, the present invention provides that the spent catalyst is obtained from different refining processes like fluid catalytic cracking process, residue fluid catalytic cracking process, high severity fluid catalytic cracking process, high severity propylene maximizing fluid catalytic cracking process, hydro processing, isomerization process or any other refinery process.

In a preferred embodiment of the present invention, the process further comprises addition of a free radical scavenger in an amount ranging from 1000-2000 ppm; wherein the free radical scavenger is an iron or cerium based compound. Preferably, the free radical scavenger is selected from iron oxide and cerium oxide.

In yet another embodiment of the present invention, the phenyl naphthalene compound obtained from the disclosed process is stable upto 450° C. on addition of the free radical scavenger.

In another embodiment of the present invention, the phenyl naphthalene compound is a heat transfer agent.

Further, the present invention provides a heat resistant formulation comprising the phenyl naphthalene compound obtained from the disclosed process and a free radical scavenger; wherein the free radical scavenger is an iron or cerium based compound.

In another embodiment, the present invention provides that the free radical scavenger is present in the heat resistant formulation in an amount ranging from 1000-2000 ppm.

Thus, the present invention exhibits the following advantages:

- The synthesis process involved use of universal solvent water as reaction medium.
- The recovered/recycled cost effective catalyst used in the process is easily available and highly economical.
- The recovered catalyst used in various refining processes is easily available and highly economical.
- The reaction medium is environmentally benign.
- The process produces product of high purity and in high yields thereby reducing purification steps and hence is cost effective process.
- Any isomerization and thermal degradation at high temperature is controlled by optimizing a formulation along with a free radical scavenger.
- The process is of single-step with no complexity involved and is easy to scale up.
- The reaction temperature is moderate (90-110° C.).
- Cost effective and highly value added products are synthesized viz. 1-phenylnaphthalene and 2-methyl-1-phenyl naphthalene.
- Using synthesized products, a heat stable formulation upto 450° C. is optimized along with free radical scavenger.

The present invention is further illustrated based on the disclosed embodiments through several non-limiting working examples.

Catalyst

Catalyst was collected from different refineries. It is Pd-carbon based catalyst. The palladium content is about 0.05 to 0.1% in the catalyst. The spent catalysts thus obtained was grinded in mortar and pestle to its powder form size prior to use. The catalyst was used without any further activation.

Dodecyl Sodium Sulphate

Commercial dodecyl sodium sulphate was used with 96% purity. This reagent acts to stabilize palladium particles from agglomeration.

Tri Potassium Phosphate

Commercial tri potassium phosphate was used with 97% purity. This component acts as base and has three different roles—(i) helps in the formation of the palladium complex, (ii) helps in the formation of the trialkyl/triaryl boron compound and (ii) accelerates the reductive elimination step by reaction of the alkoxide with the palladium complex.

Solvent

Water was used as an environmentally benign solvent. Distilled water was used as reaction medium.

PREPARATION OF THERMAL FLUID MOLECULES

Example 1

Typical Reaction Procedure: One-Pot Synthesis of 1-phenylnaphthalene from 1-bromonaphthalene and phenylboronic acid Synthesis of 1-phenylnaphthalene was carried out in a glass reactor fitted with condenser and controlled heating system. In a typical reaction process, tri potassium phosphate ($K_3PO_4$) (0.15 mol), sodium dodecyl sulfate (SDS) (0.05 mol) and spent catalyst (10 gm) were taken in a round bottom flask. 200-400 ml of water was added to the reactor and stirred. Phenylboronic acid (0.13 mol) was added to the mixture followed by 1-bromonaphthalene (0.1 mol) at room temperature. Reaction progress was monitored by thin layer chromatography (TLC). The reaction mixture was then heated at 100° C. with vigorous stirring (300-500 rpm) for 4-6 hrs. The reaction mixture was cooled to room temperature and filtered to separate the catalyst. The filtered catalyst was washed with organic solvent viz diethyl ether, ethyl acetate (30 ml) for reuse. The reaction mixture was then extracted with ethyl acetate (50 ml×3). The organic layer was separated and evaporated to obtain the products. The products were purified by distillation. The identification of the product was carried out by GC and GC-MS analysis.

Typical Reaction Procedure: One-Pot Synthesis of 2-methyl-1-phenylnaphthalene from 1-bromo-2-methylnaphthalene and phenylboronic acid Synthesis of 2-methyl-1-phenylnaphthalene was carried out in a glass reactor fitted with condenser and controlled heating system. In a typical reaction process, tri potassium phosphate ($K_3PO_4$) (0.15 mol), sodium dodecyl sulfate (SDS) (0.05 mol) and spent catalyst (10 gm) were taken in a round bottom flask. 200-400 ml of water was added to the reactor and stirred. Phenylboronic acid (0.13 mol) was added to the mixture followed by 1-bromo-2-methylnaphthalene (0.1 mol) at room temperature. Reaction progress was monitored by thin layer chromatography (TLC). The reaction mixture was then heated at 100° C. with vigorous stirring (300-500 rpm) for 4-6 hrs. The reaction mixture was cooled to room temperature and filtered to separate the catalyst. The filtered catalyst was washed with organic solvent viz diethyl ether, ethyl acetate (30 ml) for reuse. The reaction mixture was then extracted with ethyl acetate (50 ml×3). The organic layer was separated and evaporated to obtain the products. The products were purified by distillation. The identification of the product was carried out by GC and GC-MS analysis.

Catalyst Characterization

Analytical study was carried out on the powdered spent catalyst received from Purified Terephthalic Acid (PTA) unit of Refineries.

XRF Analysis

The XRF (Na—U Scan) analysis showed the presence of Pd, Cr, Mo with presence of Ti, Si, Zn, Al, Sb, S, Mg in the Refinery spent catalyst.

XRD Analysis

XRD analysis showed peaks of Pd metal (Pd lines included in plot) with some peaks (less crystalline graphitic peaks) of carbon. The XRD pattern of Refinery spent catalyst is shown in FIG. 1

Elemental Analysis

The elemental analysis of Refinery spent catalyst showed the presence of Al, Ca, Cr, Fe, K, Mg, Pd and Ti in minor amounts as 166, 95, 51, 350, 65, 39, 253 and 71 ppm level quantity respectively. Palladium metal (Pd) was present in the Refinery spent catalyst in the range of 217-253 ppm. The presence of Pd metal was also confirmed by XRF analysis. The detailed metal content of the spent catalyst are given below in the Table 1.

TABLE 1

Results of elemental analysis

| Sample Description | Aliquot Vol. | Diluted to Vol. | Analyte | Conc (ppm) |
|---|---|---|---|---|
| Refinery spent catalyst | 2.0953 | 25 | Al | 166.3 |
|  | 2.0953 | 25 | Ca | 95.2 |
|  | 2.0953 | 25 | Cr | 50.7 |

TABLE 1-continued

Results of elemental analysis

| Sample Description | Aliquot Vol. | Diluted to Vol. | Analyte | Conc (ppm) |
|---|---|---|---|---|
|  | 2.0953 | 25 | Fe | 349.7 |
|  | 2.0953 | 25 | K | 65.5 |
|  | 2.0953 | 25 | Mg | 39.0 |
|  | 2.0953 | 25 | Pd | 252.7 |
|  | 2.0953 | 25 | Ti | 71.1 |

Thermogravimetric Analysis (TGA) Analysis

Figure 2:
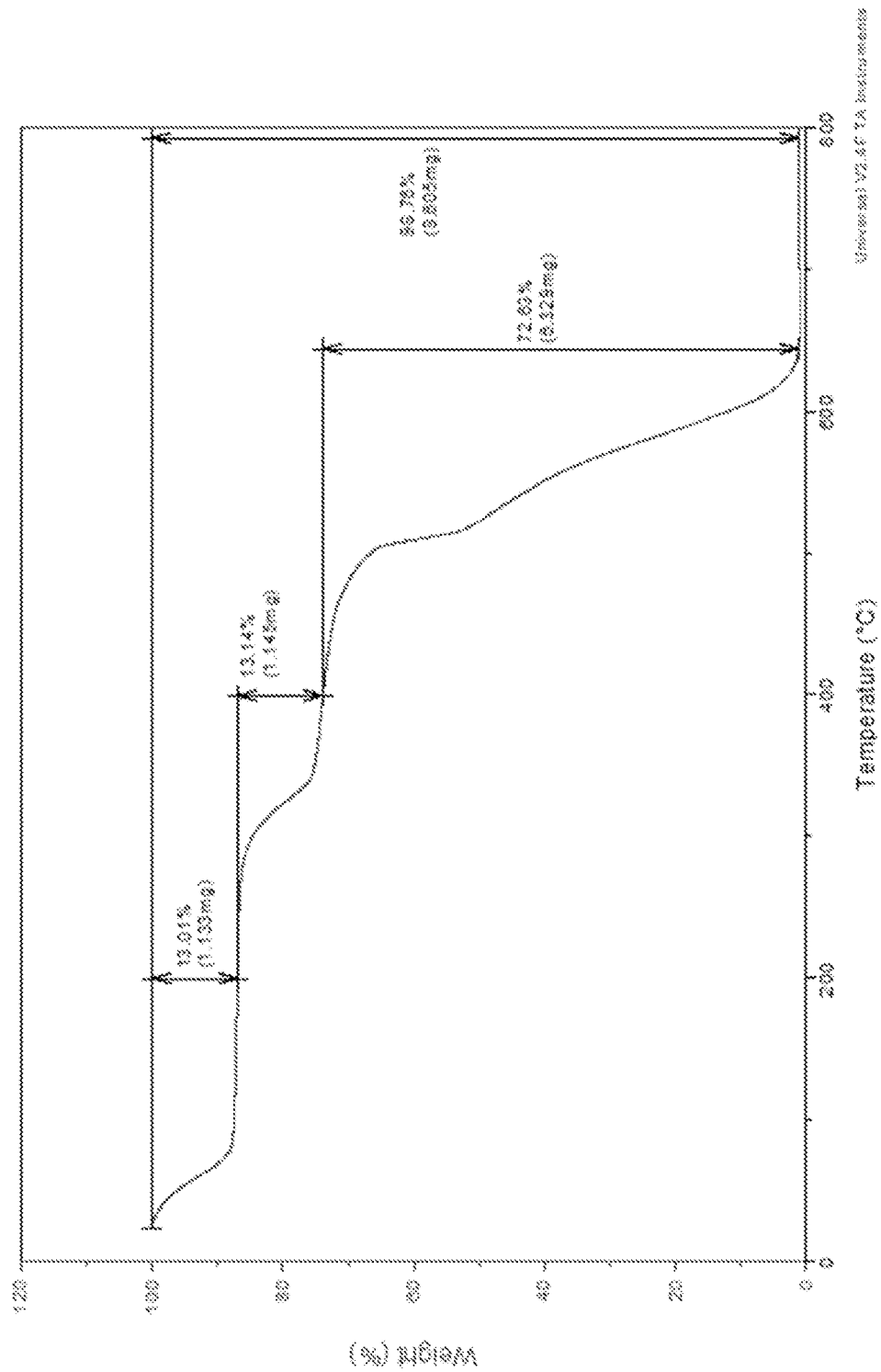
FIG. 2 represents TGA analysis of Refinery spent catalyst.

In the heterogeneous catalysts, stability of active sites on catalyst surface is very important. Thermogravimetric analysis is widely used to identify mass changes due to temperature. This method is used to characterize the presence of metal in the Refinery spent catalyst. The stability of Refinery spent catalyst was measured by Thermogravimetric analysis (TGA) on TG model 2950 Hi Resolution modulated TGA, with heating rates 10° C./min, temperature ramp up to 800° C. The results given in the FIG. 2 showed that weight loss of 13.01 wt. % was observed at 100° C. corresponding to the removal of loosely absorbed water on the surface. The decomposition of amorphous carbon at ~300° C. producing oxides of carbon associated with weight loss of 13.14 wt. %. Further the weight loss of 72.83 wt. % at 400° C.-600° C. signifies the decomposition of carbon which is crystalline in nature thereby indicating higher activity of catalyst.

Example 2

Synthesis of 1-phenyl naphthalene in Absence of Refinery Spent Catalyst

Tri potassium phosphate ($K_3PO_4$) (0.015 mol), sodium dodecyl sulfate (SDS) (0.005 mol) and 40 ml of water were taken in a round bottom flask. Phenylboronic acid (0.011 mol) was added to the mixture followed by 1-bromonaphthalene (0.01 mol) at room temperature. The reaction mixture was then heated at 100° C. with vigorous stirring for 12 hrs. Thin layer chromatography showed no reaction progress.

Example 3

Synthesis of 1-phenyl naphthalene in Absence of tri potassium phosphate and sodium dodecyl sulfate Spent catalyst 1 gm and 40 ml of water were taken in a round bottom flask. Phenylboronic acid (0.011 mol) was added to the mixture followed by 1-bromonaphthalene (0.01 mol) at room temperature in the open air. The reaction mixture was then heated at 100° C. with vigorous stirring for 12 hrs. The reaction did not occur as no changes were observed in thin layer chromatography.

Example 4

Synthesis of 1-phenyl naphthalene in Absence of tri potassium phosphate

Sodium dodecyl sulfate (SDS) (0.005 mol), spent catalyst 1 gm and 40 ml of water were taken in a round bottom flask. Phenylboronic acid (0.011 mol) was added to the mixture followed by 1-bromonaphthalene (0.01 mol) at room temperature in the open air. The reaction mixture was then heated at 100° C. with vigorous stirring for 12 hrs. No reaction progress was observed on TLC and was also confirmed by GC-MS.

Example 5

Synthesis of 1-phenyl naphthalene

Tri potassium phosphate ($K_3PO_4$) (0.015 mol), sodium dodecyl sulfate (SDS) (0.005 mol), spent catalyst (0.5 gm) and 40 ml of water were taken in a round bottom flask. Phenylboronic acid (0.011 mol) was added to the mixture followed by 1-bromonaphthalene (0.01 mol) at room temperature in the open air. The reaction mixture was then heated at 100° C. with vigorous stirring for 6 hrs. The reaction occurred but TLC shows the presence of unreacted reactants.

Example 6

Synthesis of 1-phenyl naphthalene

Tri potassium phosphate ($K_3PO_4$) (0.015 mol), sodium dodecyl sulfate (SDS) (0.005 mol), spent catalyst (1 gm) and 40 ml of water were taken in a round bottom flask. Phenylboronic acid (0.011 mol) was added to the mixture followed by 1-bromonaphthalene (0.01 mol) at room temperature in the open air. The reaction mixture was then heated at 100° C. with vigorous stirring for 4 hrs. The reaction occurred and full conversion of the reactant to product was obtained. Reaction mixture work up was carried out as described in example 1. The calculated yield of 1-phenyl naphthalene was 95% corresponding to 1-bromonaphthalene.

Example 7

Synthesis of 1-phenyl naphthalene

Tri potassium phosphate ($K_3PO_4$) (0.015 mol), sodium dodecyl sulfate (SDS) (0.005 mol), spent catalyst (1 gm) and 40 ml of water were taken in a round bottom flask. Phenylboronic acid (0.011 mol) was added to the mixture followed by 1-bromonaphthalene (0.01 mol) at room temperature in the open air. The reaction mixture was then heated at 90° C. with vigorous stirring for 6 hrs. The reaction occurred and full conversion of the reactant to product was not observed by TLC and GC.

Example 8

Synthesis of 2-methyl-1-phenyl naphthalene

Tri potassium phosphate ($K_3PO_4$) (0.015 mol), sodium dodecyl sulfate (SDS) (0.005 mol), spent catalyst (1 gm) and 40 ml of water were taken in a round bottom flask. Phenylboronic acid (0.012 mol) was added to the mixture followed by 1-bromo-2-methylnaphthalene (0.01 mol) at room temperature in the open air. The reaction mixture was then heated at 100° C. with vigorous stirring for 6 hrs. The reaction occurred and complete conversion of the reactant to product was obtained. Reaction mixture work up was carried out as described in example 1. The calculated yield of 2-methyl-1-phenyl naphthalene was 90% corresponding to 1-bromonaphthalene.

Example 9

Synthesis of 1-phenyl naphthalene

Tri potassium phosphate ($K_3PO_4$) (0.015 mol), sodium dodecyl sulfate (SDS) (0.005 mol), spent catalyst (1 gm) and 40 ml of water were taken in a round bottom flask. Phenylboronic acid (0.011 mol) was added to the mixture followed by 1-bromonaphthalene (0.01 mol) at room temperature in the open air. The reaction mixture was then heated at 90° C. with vigorous stirring for 6 hrs. The reaction was not completed (checked by TLC). Reaction mixture work up was carried out as described in example 1. The calculated yield of 1-phenyl naphthalene was 60% corresponding to 1-bromonaphthalene.

Example 10

Synthesis of 1-phenyl naphthalene

Tri potassium phosphate ($K_3PO_4$) (0.035 mol), sodium dodecyl sulfate (SDS) (0.005 mol), spent catalyst (1 gm) and 40 ml of water were taken in a round bottom flask. Phenylboronic acid (0.011 mol) was added to the mixture followed by 1-bromonaphthalene (0.01 mol) at room temperature in the open air. The reaction mixture was then heated at 100° C. with vigorous stirring for 6 hrs. The reaction occurred and complete conversion of the reactant to product was obtained. Reaction mixture work up was carried out as described in example 1. The calculated yield of 1-phenyl naphthalene was 94% corresponding to 1-bromonaphthalene.

The Catalyst can be Reused without any Major Changes in Yield as Provided Below—Thermal Study A comparative thermal stability test has been carried out under static test and dynamic test conditions. The static test was performed through Ampoule test method at 400° C. and 425° C. and the dynamic test was carried out in high pressure reactor system at different temperature viz. 400° C., 425° C., 450° C. and 500° C. The purity of both the laboratory synthesized product and commercial product was >98.1% by GC.

Static Test

The static test was carried out through Ampoule test method. In each test, 6 gm of 1-phenyl naphthalene was taken in a tube, sealed under inert atmosphere and kept at required temperature for 21 days. The test was carried out in duplicate. After completion of test the sample purity was analyzed by GC. The compounds were found very stable at 400° C. Both the commercial sample and laboratory synthesized products were found at a very good condition (purity of ~95% by GC) after the test. However, some migration/isomerization of 1-phenyl naphthalene to 2-phenyl naphthalene was observed when the static test was carried out at 425° C. for the commercial as well as laboratory synthesized products.

Dynamic Test

Dynamic test was carried out in high pressure reactor system at different temperatures in the range of 400-500° C. 50 gm of 1-phenyl naphthalene was taken in the reactor vessel, closed under nitrogen pressure of 5-10 bar. The sample was heated under stirring condition (200 rpm) at different designed temperatures for 5-6 hrs. After completion of test, the sample purity was analyzed by GC. The product was stable at 400° C.-450° C., however product isomerization was observed at temperature above 450° C. Migration of 1-phenyl naphthalene to 2-phenyl naphthalene was observed at temperature of 425° C. So, in order to arrest this migration, radical scavenger was added. Scavenger of different chemistries like Fe, Ce, Zr metal based were tried and addition of 1000-2000 ppm of Fe based radical scavenger stopped the migration of 1-phenyl naphthalene to 2-phenyl naphthalene under similar test conditions. 1-phenyl naphthalene was found stable up to 425° C. in the presence of radical scavenger. ~96% by GC for pure 1-phenyl naphthalene was observed after the dynamic test at 425° C.-450° C. under nitrogen pressure. The test was carried out in duplicate. Further stability studies were conducted at more than 450° C. The optimized formulation of phenyl naphthalenes with optimized dosages of free radical scavenger were found to be stable upto 450° C.

We claim:

1. A one-pot process of synthesis of a phenyl naphthalene compound, wherein the process comprises:
   a) grinding a spent catalyst obtained from a refining process;
   b) mixing the spent catalyst with tripotassium phosphate and sodium dodecyl sulfate to obtain a reaction mixture I, wherein molar ratio of mixing the tripotassium phosphate and the sodium dodecyl sulfate ranges from 1:1 to 7:1;
   c) adding water to the reaction mixture I followed by stirring to obtain a reaction mixture II;
   d) adding phenylboronic acid to the reaction mixture II followed by addition of a bromonaphthalene derivative at room temperature to obtain a reaction mixture III, wherein molar ratio of mixing the phenylboronic acid and the bromonaphthalene derivative ranges from 1:1 to 1.5:1;
   e) heating the reaction mixture III followed by vigorous stirring for 4-6 hours; and
   f) cooling down to room temperature followed by filtration to separate the catalyst from a synthesis product comprising the phenyl naphthalene.

2. The process as claimed in claim 1, wherein in step (e) the reaction mixture III is heated at a temperature ranging from 90-110° C.

3. The process as claimed in claim 1, wherein the phenyl naphthalene compound is selected from 1-phenylnaphthalene and 2-methyl-1-phenylnaphthalene.

4. The process as claimed in claim 3, wherein the bromonaphthalene derivative in step (d) in the process of preparation of 1-phenylnaphthalene is 1-bromonaphthalene.

5. The process as claimed in claim 3, wherein the bromonaphthalene derivative in step (d) in the process of preparation of 2-methyl-1-phenylnaphthalene is 1-bromo-2-methylnaphthalene.

6. The process as claimed in claim 1, wherein stirring in step (e) is carried out at a speed ranging from 300-500 rpm.

7. The process as claimed in claim 1, wherein the spent catalyst is a palladium-carbon based catalyst with palladium content ranging from 0.05 to 0.1 wt % of the catalyst.

8. The process as claimed in claim 1, wherein the refining process is fluid catalytic cracking process, resid fluid catalytic cracking process, high severity fluid catalytic cracking process, high severity propylene maximizing fluid catalytic cracking process, hydro processing, or an isomerization process.

9. The process as claimed in claim 1, wherein the process further comprises addition of a free radical scavenger in an amount ranging from 1000-2000 ppm.

10. The process as claimed in claim 9, wherein the free radical scavenger is an iron or cerium based compound selected from iron oxide and cerium oxide.

11. The process as claimed in claim 9, wherein the phenyl naphthalene compound is stable upto 450° C. on addition of the free radical scavenger.

12. The process as claimed in claim 1, wherein the phenyl naphthalene compound is comprised, mixed, or used as a heat transfer agent.

13. A heat resistant formulation comprising the phenyl naphthalene compound obtained from the process as claimed in claim 1 and a free radical scavenger; wherein the free radical scavenger is an iron or cerium based compound.

14. The formulation as claimed in claim 13, wherein the free radical scavenger is present in an amount ranging from 1000-2000 ppm.

* * * * *